United States Patent [19]
Alexander

[11] Patent Number: 5,910,146
[45] Date of Patent: *Jun. 8, 1999

[54] DEVICE FOR ASSISTING CHILDBIRTH

[75] Inventor: Gary E. Alexander, Baton Rouge, La.

[73] Assignee: Medisys Technologies, Inc., Baton Rouge, La.

[*] Notice: This patent is subject to a terminal disclaimer.

[21] Appl. No.: 08/863,921

[22] Filed: May 27, 1997

Related U.S. Application Data

[63] Continuation-in-part of application No. 08/413,125, Mar. 29, 1995, Pat. No. 5,632,750, which is a continuation-in-part of application No. 08/250,054, May 27, 1994, Pat. No. 5,593,413, which is a continuation-in-part of application No. 08/036,560, Mar. 25, 1993, Pat. No. 5,318,573, which is a continuation-in-part of application No. 07/982,016, Nov. 24, 1992, Pat. No. 5,217,467, and a continuation of application No. 07/851,068, Mar. 13, 1992, abandoned, which is a continuation-in-part of application No. 07/522,592, May 14, 1990, Pat. No. 5,122,148.

[51] Int. Cl.⁶ .................................................. A61B 17/00
[52] U.S. Cl. ........................... 606/122; 606/121; 606/119
[58] Field of Search .................................... 606/122, 121, 606/119, 1

[56] References Cited

U.S. PATENT DOCUMENTS

| | | | |
|---|---|---|---|
| 13,453 | 8/1855 | Buffum | 606/122 |
| 713,166 | 11/1902 | St. Cyr . | |
| 1,690,942 | 11/1928 | Odell . | |
| 1,782,814 | 11/1930 | Froehlich . | |
| 2,618,272 | 11/1952 | Larson | 606/122 |
| 3,139,886 | 7/1964 | Tallman et al. . | |
| 3,550,595 | 12/1970 | Laufe . | |
| 3,605,748 | 9/1971 | Salinas-Benavides | 128/323 |
| 3,665,925 | 5/1972 | Dersookian | 128/323 |
| 3,785,381 | 1/1974 | Lower et al. | 128/323 |
| 3,789,849 | 2/1974 | Laufe et al. | 128/323 |
| 3,794,044 | 2/1974 | Vennard et al. | 128/352 |
| 4,597,391 | 7/1986 | Janko | 128/361 |
| 4,875,482 | 10/1989 | Hariri et al. | 128/352 |
| 5,122,148 | 6/1992 | Alexander | 606/122 |
| 5,207,687 | 5/1993 | Bernon | 606/122 |
| 5,217,467 | 6/1993 | Alexander | 606/122 |
| 5,318,573 | 6/1994 | Alexander | 606/122 |
| 5,593,413 | 1/1997 | Alexander | 606/122 |
| 5,632,750 | 5/1997 | Alexander et al. | 606/122 |

FOREIGN PATENT DOCUMENTS

| | | |
|---|---|---|
| 669116 | 10/1993 | Australia . |
| WO 89/11253 | 11/1989 | France . |
| 2233840 | 6/1977 | Germany . |
| 2925386 | 6/1979 | Germany . |

*Primary Examiner*—Richard J. Apley
*Assistant Examiner*—Benjamin K. Koo
*Attorney, Agent, or Firm*—Roy, Kiesel & Tucker, PLC

[57] ABSTRACT

A device to assist in removing a fetus from a woman's birth canal during childbirth is provided. The device includes a pliable, elongated member having a mouth adapted to fit over the head of a fetus, an insertion wand or applicator for positioning the elongated member over the head of the fetus, and a drawstring attached at the mouth. The elongated member is constructed so that as it is pulled longitudinally from the end opposite the mouth, the elongated member will axially grip the head of the fetus in much the same way that the novelty item, "Chinese handcuffs," grip the finger of a user. Once the elongated member has axially engaged the head of the fetus, the elongated member may be used to extract the fetus from the birth canal.

28 Claims, 19 Drawing Sheets

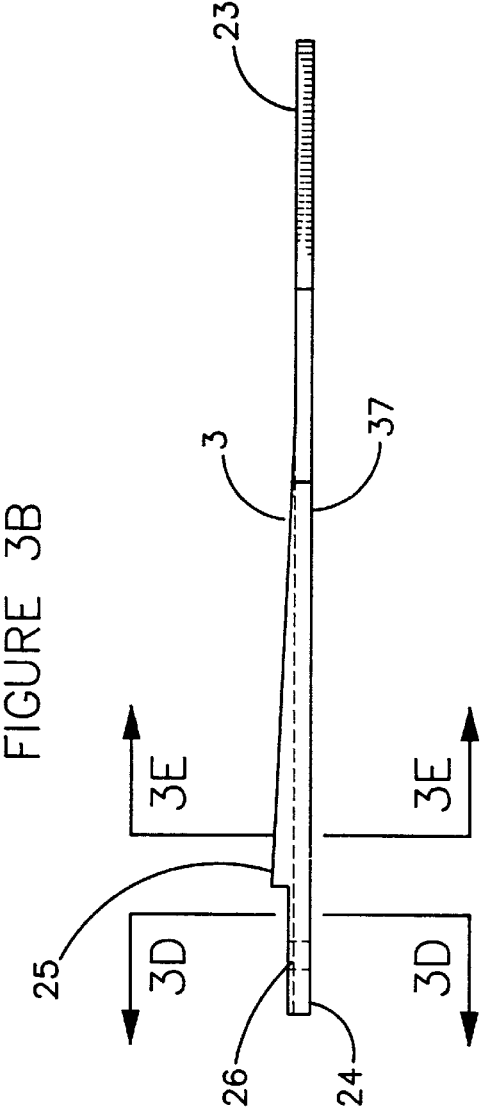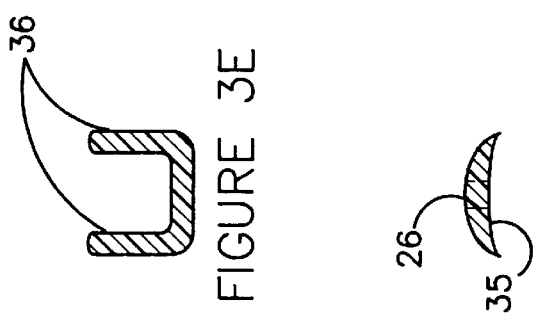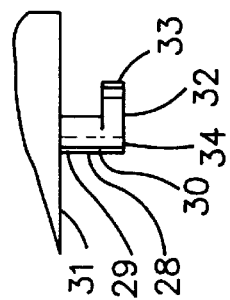

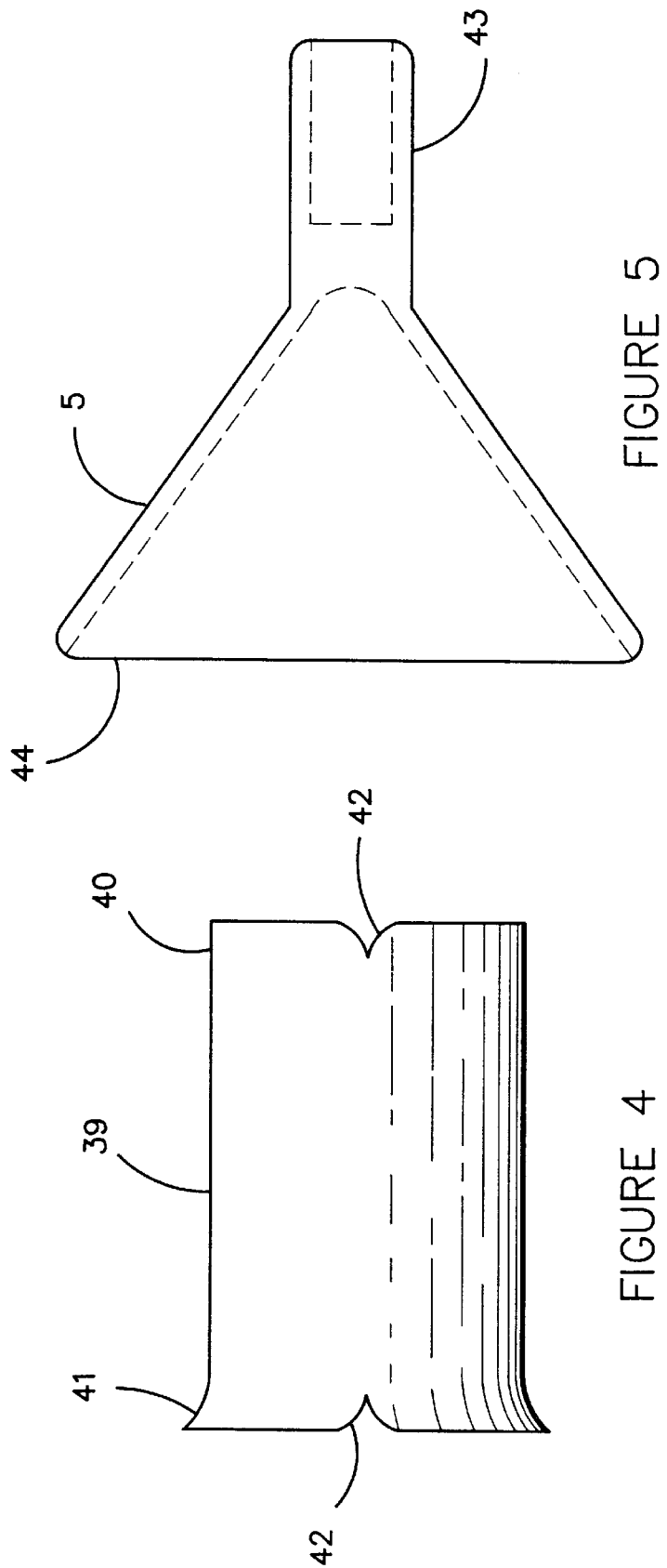

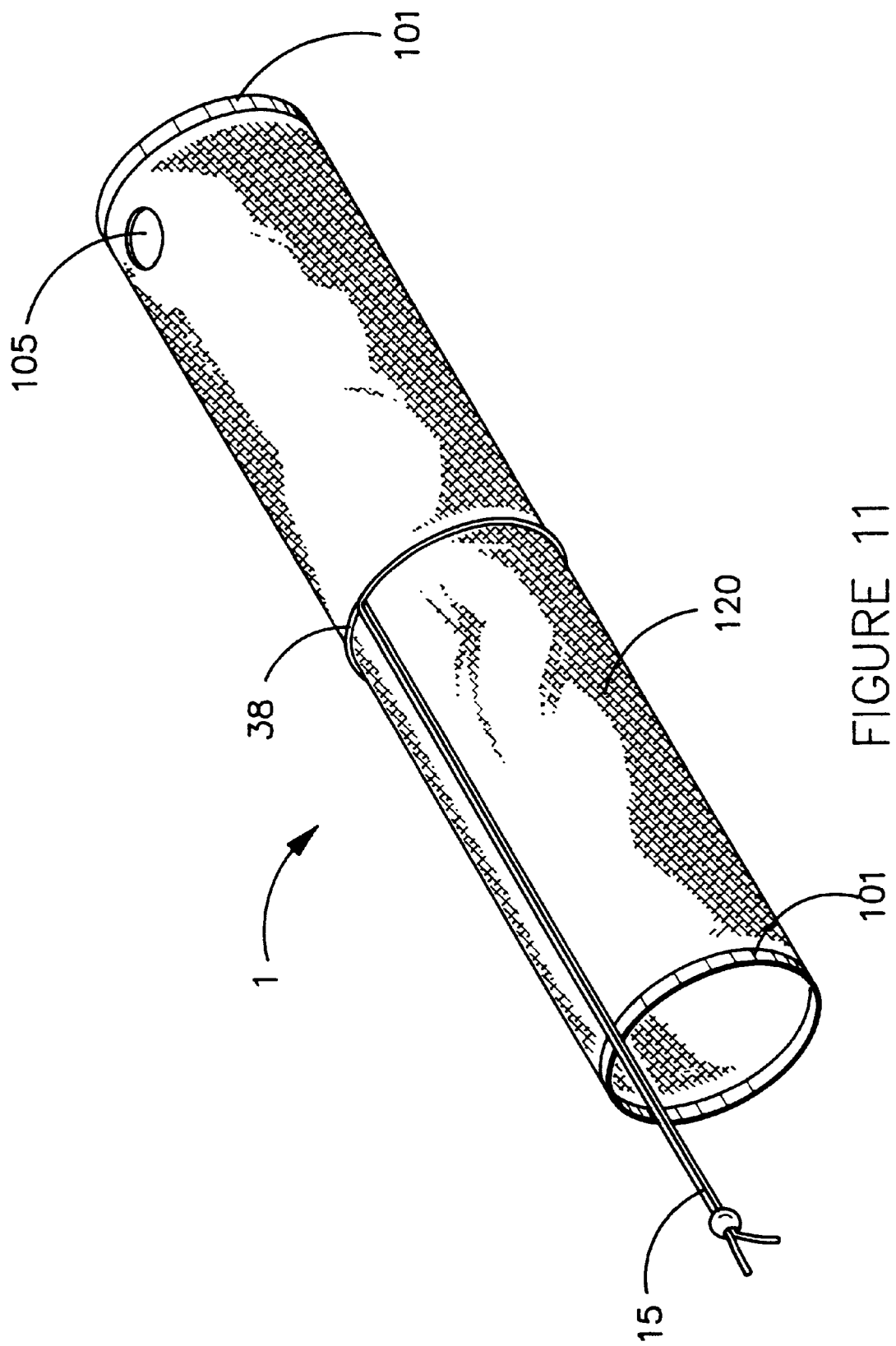

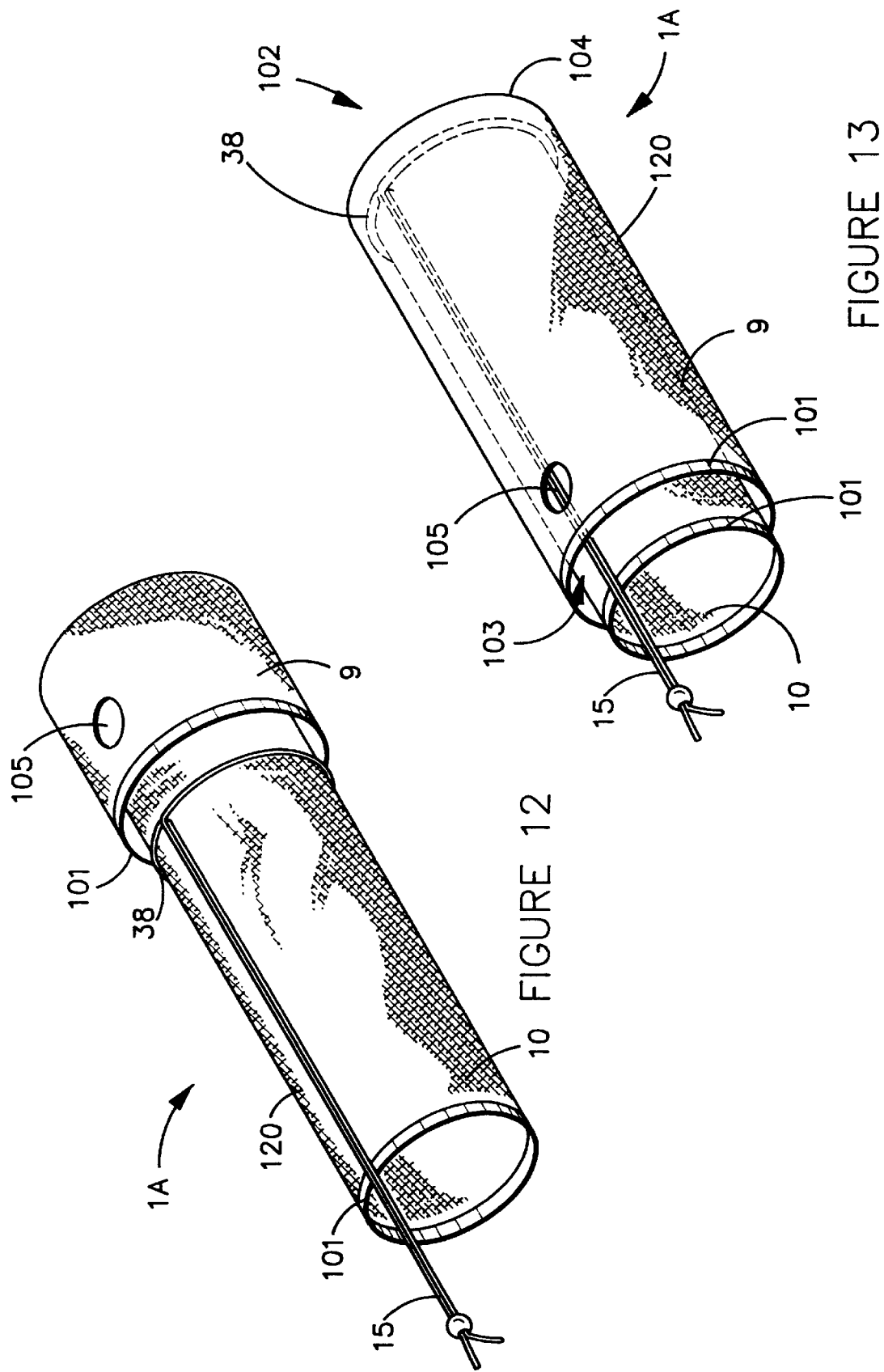

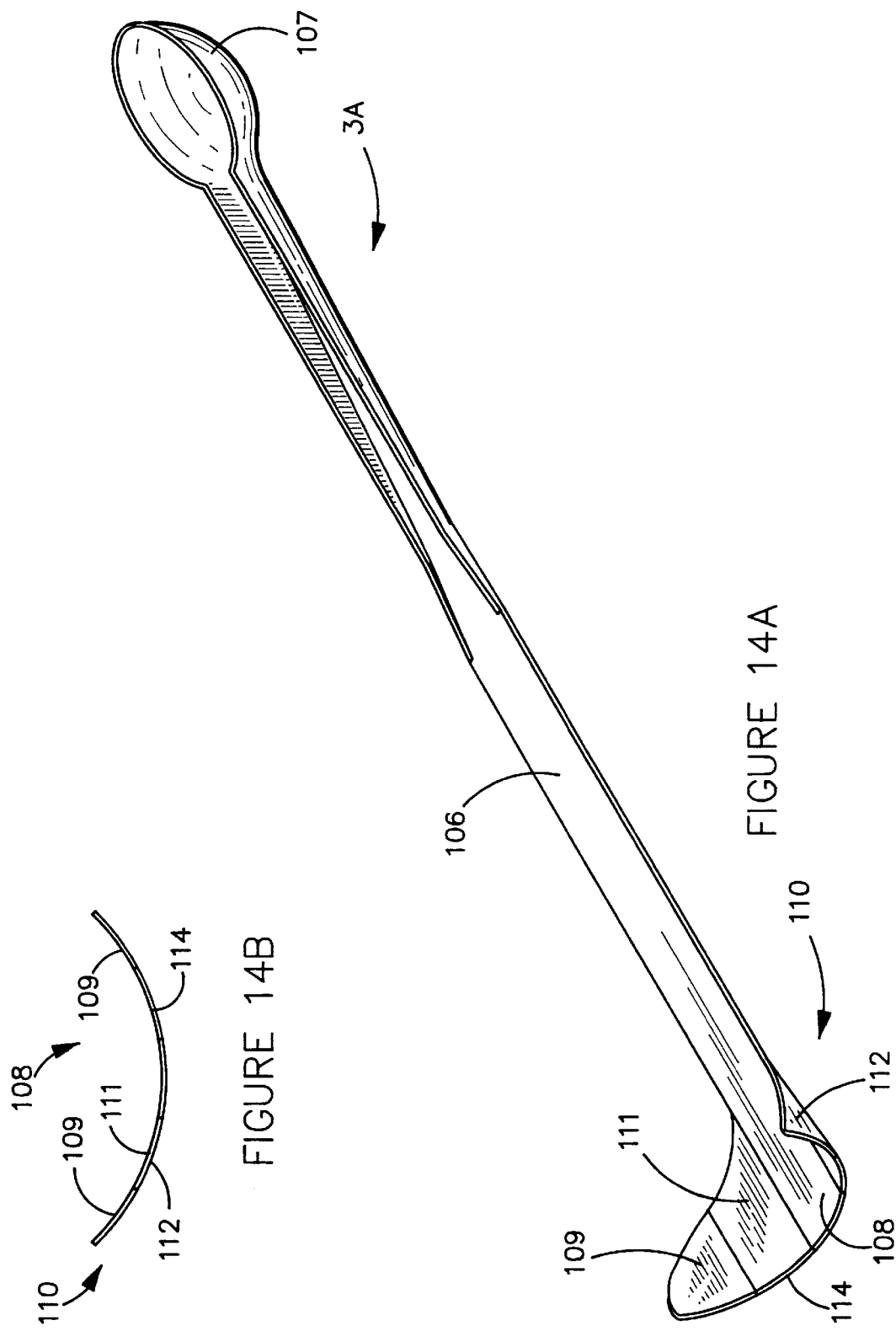

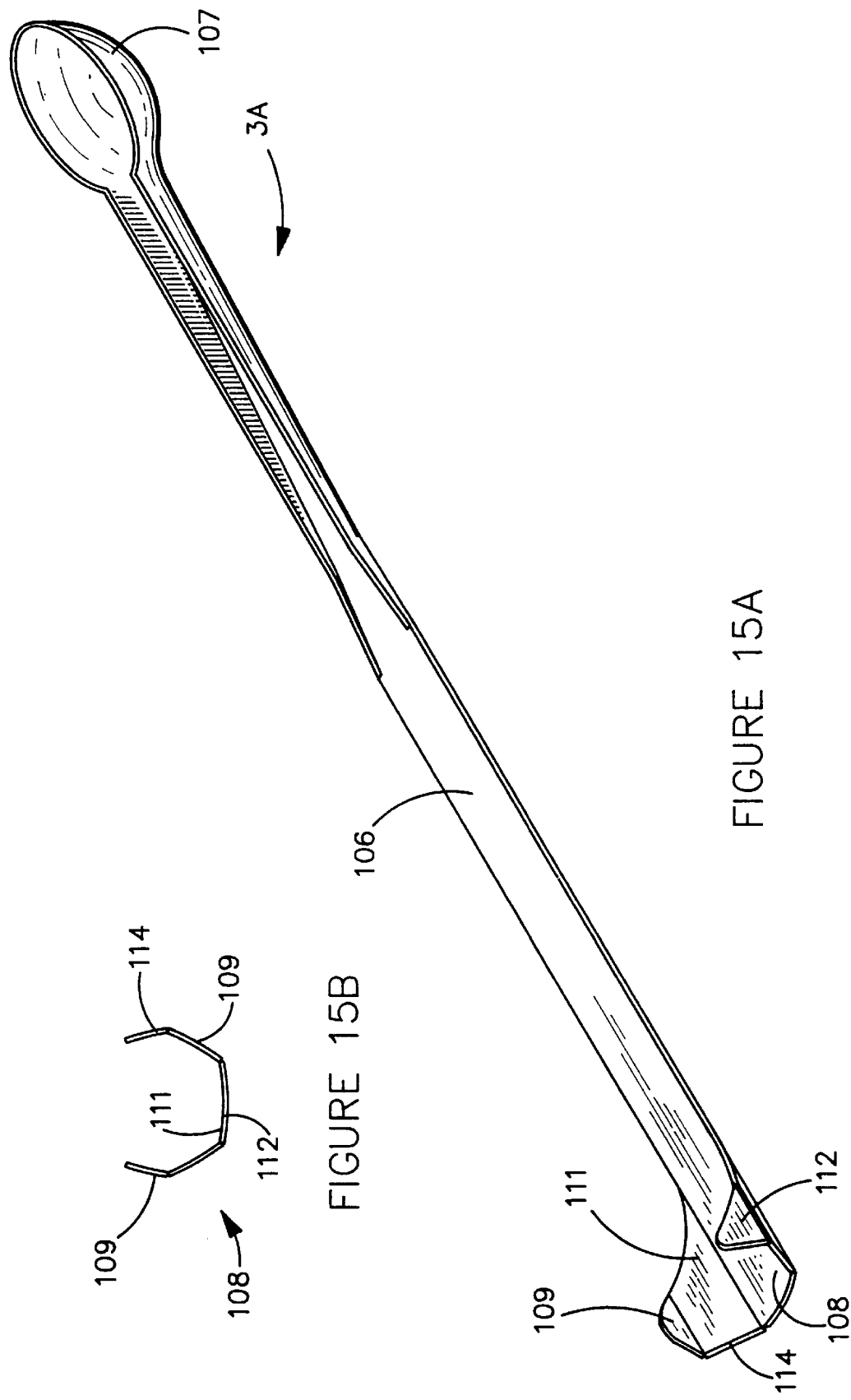

ly delivery. The devices used in the prior art have two principal subcategories: forceps and vacuum extraction. In the case of severe cephalo-pelvic disproportion, placenta previa, vaso previa, and other contraindications to vaginal delivery, the "C-Section," whether classic or low transverse, remains the mainstay procedure. However, it has long been recognized that to the extent that C-Section deliveries can be successfully avoided, statistical. maternal and fetal benefits will be realized. Even the non-difficult vaginal delivery can benefit from non-traumatic assists.
DEVICE FOR ASSISTING CHILDBIRTH

CROSS-REFERENCE

This is a continuation-in-part application of a U.S. patent application Ser. No. 08/413,125, filed on Mar. 29, 1995, and which will issue as U.S. Pat. No. 5,632,750, on May 27, 1997, which was a continuation-in-part application of U.S. patent application Ser. No. 08/250,054, filed on May 27, 1994 now U.S. Pat. No. 5,593,413, which is a continuation-in-part application of a U.S. patent application Ser. No. 08/036,560, filed on Mar. 25, 1993, now U.S. Pat. No. 5,318,573, which is a continuation-in-part application of U.S patent application Ser. No. 07/982,016, filed on Nov. 24, 1992, now U.S. Pat. No. 5,217,467, which was a file wrapper continuing application of U.S. patent application Ser. No. 07/851,068, filed on Mar. 13, 1992, now abandoned, which was a continuation-in-part application of U.S. patent application Ser. No. 07/522,592, filed on May 14, 1990, now U.S. Pat. No. 5,122,148, all of which are hereby incorporated by reference.

BACKGROUND OF THE INVENTION

1. Field of the Invention

This invention relates in general to obstetric devices, and more particular to devices useful in removing the fetus during vaginal delivery.

2. Prior Art

Today's state of the art obstetrics utilizes various procedures to assist in instances of difficult vaginal deliveries. These procedures basically fall into three categories: version, Caesarian, and device assisted delivery. The devices used in the prior art have two principal subcategories: forceps and vacuum extraction. In the case of severe cephalo-pelvic disproportion, placenta previa, vaso previa, and other contraindications to vaginal delivery, the "C-Section," whether classic or low transverse, remains the mainstay procedure. However, it has long been recognized that to the extent that C-Section deliveries can be successfully avoided, statistical. maternal and fetal benefits will be realized. Even the non-difficult vaginal delivery can benefit from non-traumatic assists.

Many problems may develop during delivery which require assistance from the attending obstetrician to successfully remove the baby from the birth canal. One such problem results from the presenting part of the baby, usually its head, descending too slowly. This is particularly true in the case of the primigravida mother. Even with a completely dilated and effaced cervix, and an adequate pelvis, a fetus might refuse to descend beyond station "+1", especially when the mother is suffering from contraction exhaustion. Slow descent remains a problem even with an assist from administration of oxytocin (Pitocin). The problem of slow descent can also be exacerbated by anesthesia, especially epidural anesthesia, which frequently produces induced non-beneficial partial atony of the engaged and dedicated muscles. Such partial atony frequently results in non-beneficial, and sometimes hazardous, prolongation of labor.

Forceps are limited by the stage of delivery at which they may be safely applied. Station "+1" is considered mid-pelvis and in the usual case is considered too high for a forceps-assisted delivery. The risks to the fetus with forceps application at this level are extreme. Forceps cannot be safely used until the presenting part is at least at station "+2", and preferably between stations "+2" and "+3", which is the floor of the perineum. Modern obstetrics has not developed an alternative to the use of forceps when an assisted natural delivery is indicated, such as when the fetus is consistently exhibiting late decelerations of heartbeat following contractions or is exhibiting non-variability of the baseline heartbeat rate.

Obstetrical forceps are typically, in their various types, two-bladed instruments which are blindly inserted one blade at a time in a hopefully temporal-cheek position and then articulated together before assisting traction is applied. Actual traction is exerted slightly below or underneath the mandible. Traction applied with forceps is point concentrated and slippage of the forceps is increased because of natural lubrication, refusal of the fetal skull to conform to existing forceps design, and other known myriad of variables that vary from one fetus-to-pelvis physical relationship to another.

Even proper positioning of the forceps can result in harm to the fetus. For example, in instances of minimal cephalo-pelvic disproportion, the insertion of one blade of the forceps can exacerbate any slight deficiency in birth canal adequacy. In addition the softness, or pliability, of the fetal skull, coupled with the existence of sutures which separate the plates of the skull, render the skull susceptible to trauma associated with metal forceps assisted deliveries.

In an attempt to alleviate the potential trauma of forceps, vacuum extractors have seen some use. Devices which use cloth or other pliable materials which envelope the fetal head have also been developed. However, because these devices are pliable, insertion of these devices can be problematic or slow. What is needed is a device for assisting childbirth which is safe for the mother and the fetus and which overcomes the shortcomings of the prior art.

OBJECTS OF THE INVENTION

It is therefore an object of this invention to provide an assisting device for childbirth which can safely perform substantially all of the functions of forceps and vacuum extractors without the risks inherent in the use of these devices.

Another object of this invention is to provide an assisting device for childbirth that is easy to use and reduces the risk of injury to the fetus during childbirth.

Still another object of this invention is to provide an assisting device for childbirth that can be quickly applied to the head of the fetus by the attending physician.

Still other objects and advantages of this invention shall become apparent from the ensuing descriptions of the invention.

SUMMARY OF THE INVENTION

A device for assisting the delivery of a fetus is provided. The device includes a sock-like elongated cylindrical member having an open first end sized to fit over and surround the fetal head. Two or more pliable sheaths are spaced around the elongated member and attached at its open end. Semi-rigid insertion wands fit into the sheaths and are used to push the elongated member over the fetal head. The insertion wands are attached at their proximal ends to a rigid hollow insertion handle, so that the operator of the apparatus can apply force to all of the wands by simply pushing on the insertion handle. An application cone engages the fetal head and guides the elongated member's open over the fetal head. Pressure is maintained on the cone by the use of an application rod which is attached to the application cone. The proximal end of the application rod fits through and protrudes from the insertion handle. An insertion sleeve is used to compress the open first end of the elongated member and the insertion wands for the initial insertion of the device into the introitus. The elongated member also includes a drawstring which keeps the elongated member over the fetal head until axial gripping of the fetal head by the elongated member can be initiated.

It is an advantage of the invention that it can be operated by only one person, with surgical shears being the only additional equipment required.

It is a further advantage of the invention that the apparatus is of minimal thickness and fits easily between the fetal head and the birth canal.

BRIEF DESCRIPTION OF THE DRAWINGS

FIG. 3A shows a side view of a single insertion wand forming part of this invention.

FIG. 3B shows the insertion handle with a single attached insertion wand forming part of this invention.

FIG. 3C is an enlarged view of a single catch forming part of this invention.

FIG. 3D is a sectional view of an insertion wand taken along view line 3D in FIG. 3A.

FIG. 3E is a sectional view of an insertion wand taken along view line 3E in FIG. 3A.

FIG. 4 shows a side view of a preferred embodiment of the insertion sleeve forming part of this invention.

FIG. 5 shows a side view of the application cone forming part of this invention.

FIG. 11 is a perspective view of a preferred embodiment of elongated member having a drawstring and a window.

FIG. 12 is a perspective view of the preferred embodiment of elongated member shown in FIG. 11 wherein the elongated member is being folded back upon itself to create an inner layer and an outer layer.

FIG. 13 is a perspective view of the preferred embodiment of elongated member shown in FIG. 12 wherein the outer layer has been folded back sufficiently to position the drawstring looped portion at one end of the folded elongated member.

FIG. 14A is a perspective view of a preferred embodiment of an insertion wand wherein the hinged sections of the application end are in their fully extended position.

FIG. 14B is an end view of a preferred embodiment of the application end of an insertion wand wherein the hinged section of the application end are in their fully extended position.

FIG. 15A is a perspective view of a preferred embodiment of an insertion wand wherein the hinged sections of the application end are not in their fully extended position.

FIG. 15B is an end view of a preferred embodiment of the application end of an insertion wand wherein the hinged section of the application end are not in their fully extended position.

DETAILED DESCRIPTION

Figure 1:
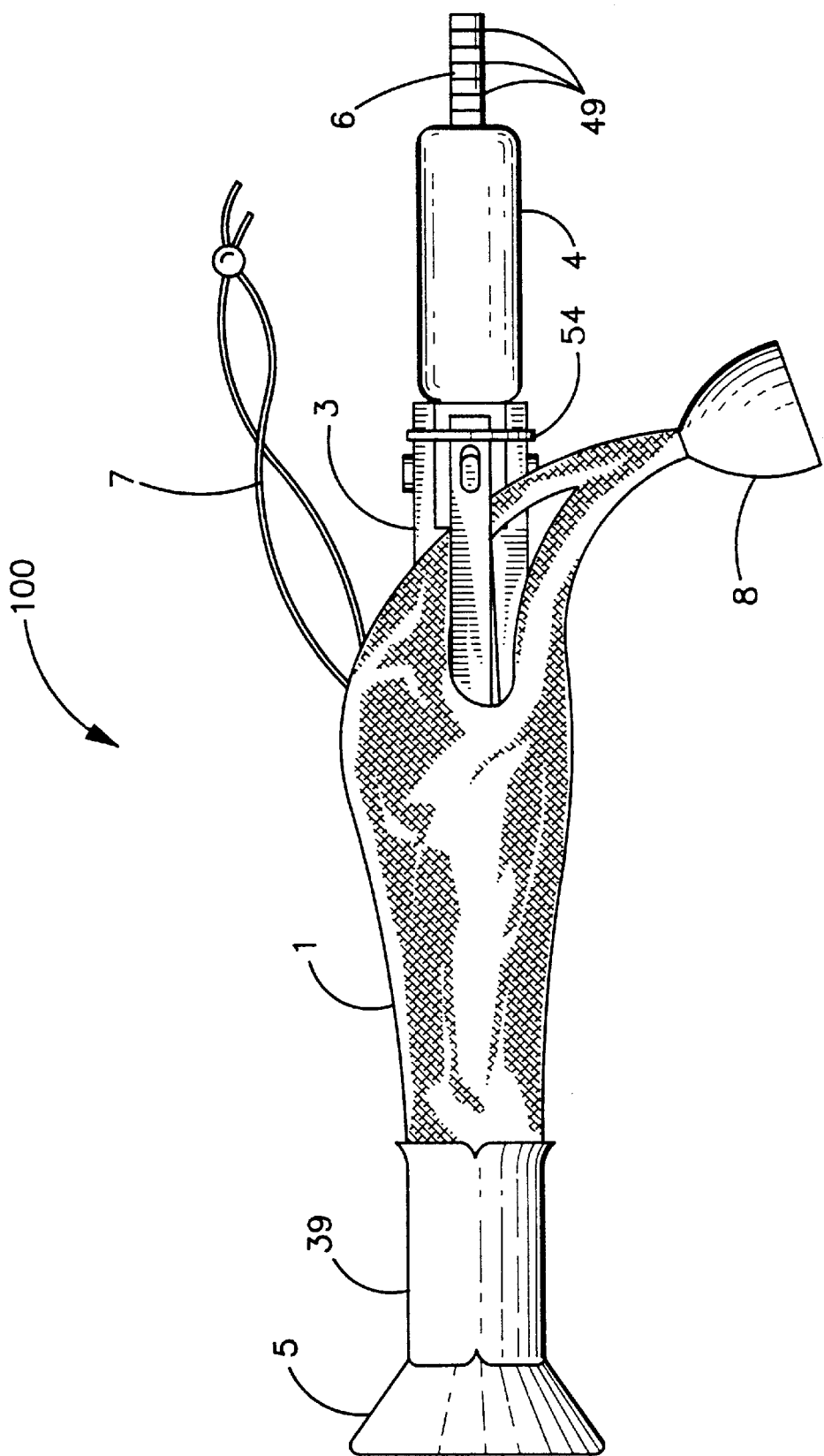
FIG. 1 is a perspective view of the apparatus as it appears when shipped and ready for use.

FIG. 1 is a perspective view of the device for assisting childbirth 100 with all components. The device includes elongated member 1, wand sheaths 2 (not shown), insertion wands 3, insertion handle 4, application cone 5, application rod 6, restricting means 7, and traction handle 8.

Figure 2:
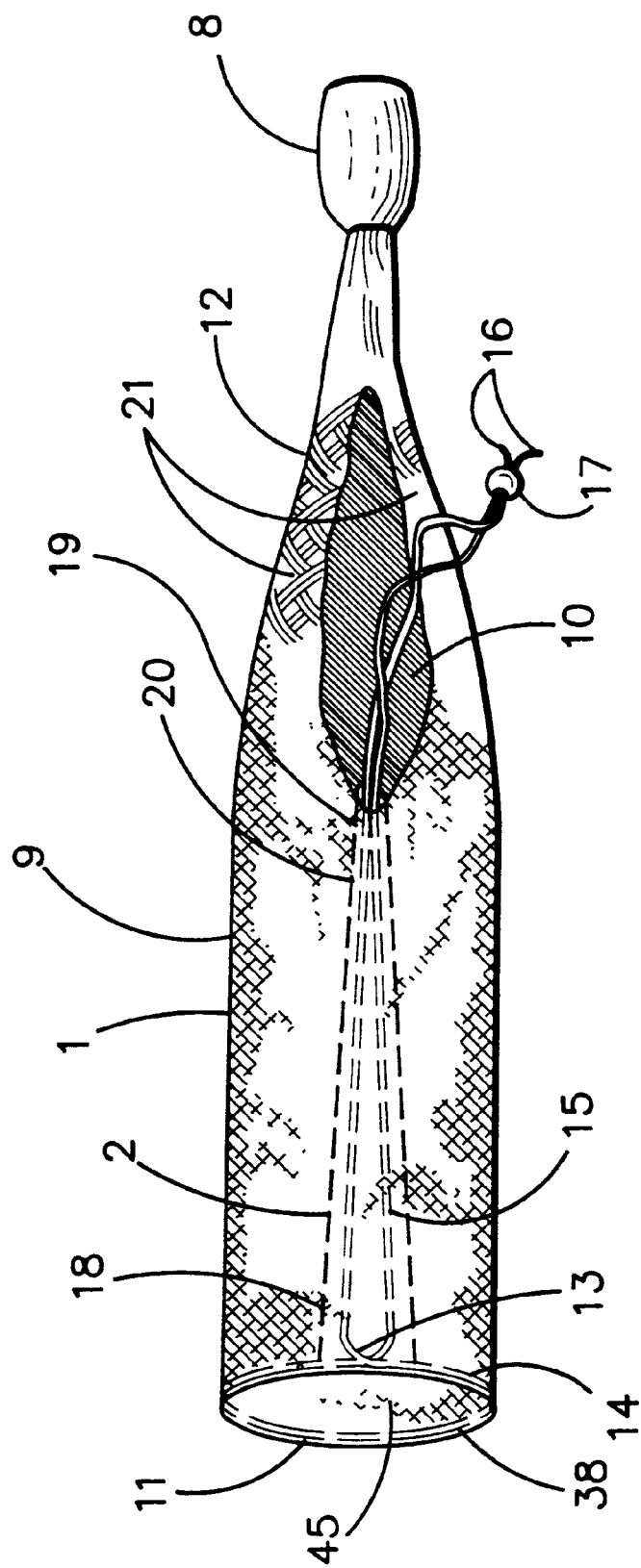
FIG. 2 is a perspective view of the elongated member forming part of this invention.

Referring to FIG. 2, elongated member 1 is depicted. Elongated member 1 includes open first end 11 and second end 12 which are connected by passageway 45. Elongated member 1 will be formed of a braid material. As depicted in FIG. 2, for the preferred embodiment a double-layered elongated member is formed by extruding a continuous cylindrical member and then folding the cylindrical member so that outer layer 9 and inner layer 10 are formed. One could terminate the braid material by cutting it at open first end 11 and sewing or binding together the fibers. However, it is preferred to terminate the braid material by folding it to form a double-layered member. Compared to a single-layered member, a double-layer member exhibits enhanced axial gripping qualities and is easier to manufacture.

The braid material is constructed by loosely weaving series of strands in an over and under manner. In the embodiment depicted the series use monofilament strands 120, such as fishing line, with a thickness of six/one-thousandths of an inch. The strands are in a parallel series of five each; however, one skilled in the art could construct the device with more or fewer strands in each series. Also, although in the embodiment depicted the braid material is constructed of monofilament fibers, one skilled in the art could construct the braid material from any material or fibers which would allow elongated member 1 to exhibit axial gripping.

Restricting means 13 for tightening said open first end about the neck and head of the fetus is generally located at open first end 11. Restricting means 13 includes drawstring sleeve 14, which can be an enveloping structure such as a nylon cloth tube, and drawstring 15. Although in the embodiment depicted, drawstring sleeve 14 is a nylon tube, one could route drawstring 15 through loops attached to open first end 11, could weave drawstring 15 through the braid material, or could use any other means capable of causing drawstring 15 to cooperate with open first end 11 so as to tighten open first end 11 around the fetal head when drawstring 15 is pulled.

Drawstring ends 16 are held together by fastener 17. As can be seen in FIG. 2, drawstring 15 is looped around open first end 11 within drawstring sleeve 14 such that drawstring looped portion 38 constitutes part of restricting means 13. Thus, as drawstring 15 is pulled, generally from the fastener 17, drawstring looped portion 38 will decrease in size, which in turn will decrease the size of the opening at open first end 11.

A plurality of wand sheaths 2 are also provided, although in FIG. 2 only one such sheath is shown in phantom. Wand sheaths 2 are positioned between outer layer 9 and inner layer 10. Drawstring 15 can be routed from open first end 11 to second end 12 via one of the wand sheaths 2. In a particularly preferred embodiment, four wand sheaths 2 are positioned equidistantly about elongated member 1. Each wand sheath 2 is a pliable elongated nylon pocket with terminal end 18 and receiving end 19. Wand sheath 2 need only be attached to elongated member 1 at one point, although one skilled in the art could provide more attachment points.

In the embodiment depicted in FIG. 2, wand sheath 2 will be attached to elongated member 1 at sheath attachment point 20, which is generally where the braid material of elongated member 1 is no longer woven, which is also the beginning of pigtails 21. Wand sheath 2 is only attached to one layer of elongated member 1, so as to promote axial gripping secondary to traction and to allow the device to be peeled from the fetal head if the device has to be removed before delivery. Although sheaths 2 are depicted as extending to the openings formed by pigtails 21, elongated member 1 could be completely closed at second end 12, and sheaths 2 could be attached at buttonhole slits made in elongated member 1.

As seen in FIG. 2, the point where elongated member 1 is no longer woven branches out into a plurality of pigtail branches 21 which are joined together at traction handle 22. Traction handle 22 is used to hold pigtails 21 together and provides a place for the operator, generally a physician, to grab hold and exert a pulling force. Traction handle 22 can be of any shape suitable for gripping.

Referring now to FIG. 3A–3E, the preferred embodiments of insertion wands 3 and insertion handle 4 are depicted. Insertion wand 3 is semi-rigid and made of high impact plastic. Insertion wand 3 has distal end 23 and proximal end 24. As shown in FIG. 3A, insertion wand 3 presents a profile twice as thick at handle stop 25 as at wand proximal end 24. Insertion wand 3 has aperture 26 between handle stop 25 and wand proximal end 24.

Referring to FIG. 3B, insertion handle 4 is a hollow tube having exterior surface 31, grip section 48, and a tunnel (not shown) running along its entire length. A plurality of rigid catches 27 are distributed equidistantly around exterior surface 31. In the embodiment shown, there are four catches 27, although one skilled in the art could practice the invention with two or more catches and a corresponding number of wands and sheaths. Each catch 27 is L-shaped so as to engage aperture 26 on insertion wand 3 so that insertion wand 3 will remain attached to insertion handle 4 as the operator pushes the device 100 into the introitus of the mother using insertion handle 4. The device may also include elastic band 54, as shown in FIG. 1, to ensure that insertion wands 3 remain attached to insertion handle 4.

FIG. 3C is an enlarged view of catch 27 showing radial section 28 which is attached to exterior surface 31 at radial section proximal end 29. Radial section 28 extends radially outward from section proximal end 29 and terminates at radial section distal end 30. Radial section 28 has a length approximately equal to the thickness of insertion wand 3 at wand proximal end 24.

Catch 27 also has axial section 32 which has free end 33 and corner end 34. Corner end 34 is attached to radial section distal end 30 at about a 90° angle. Axial section 32 extends from corner end 32 in a direction toward wand distal end 23 and parallel to the long axis of insertion handle 4 and terminates in free end 33. As shown in FIG. 3E, axial section 32 is shaped to match with the shape of aperture 26 in insertion wand 3.

FIG. 3D is a sectional view of insertion wand 3 along view line 3D of FIG. 3A. Shown are aperture 26 and first arcuate surface 35. First arcuate surface is shaped to match with the curvature of exterior surface 31 of insertion handle 4.

FIG. 3E is a sectional view of insertion wand 3 along view line 3E of FIG. 3A. Handle stop 25 is formed by two raised portions 36. As shown by FIG. 3A, raised portions 36 taper down in size along the length of insertion wand 3 away from wand proximal end 24. Insertion wand is substantially flat by wand midpoint 37 so that insertion wand will be easier to fit between the fetal head and the wall of the birth canal. At wand distal end 23, insertion wand 3 must be thin enough to be pliable, yet thick enough to retain longitudinal strength.

FIG. 4 depicts a preferred embodiment of insertion sleeve 39, which is a hollow pliable tubular member of clear plastic. Insertion sleeve has sleeve first end 40 which may be straight or may be flared radially inward. Sleeve first end 40 is the end which will be introduced into the introitus of the mother. Sleeve second end 41 may be flared radially outward as shown, or be straight like sleeve first end 40. The size of insertion sleeve 39 is adapted such that insertion sleeve 39 will fit over open first end 11 of elongated member 1, with insertion wands 3 contained therein, and constrict said open first end to a size sufficient to allow insertion of open first end 11 into the birth canal of the mother.

Insertion sleeve 39 is made of a material which may be cut easily with surgical shears. Insertion sleeve 39 may also include shear notches 42, which are cutouts at sleeve first end 40 and second end 41.

FIG. 5 depicts application cone 5, which is a pliable resilient member having cone attachment end 43 and cone open end 44. Cone 5 is adapted to fit within open first end 11 and passageway 45 of elongated member 1. Cone 5 serves to guide open first end 11 over the fetal head.

Figure 6:
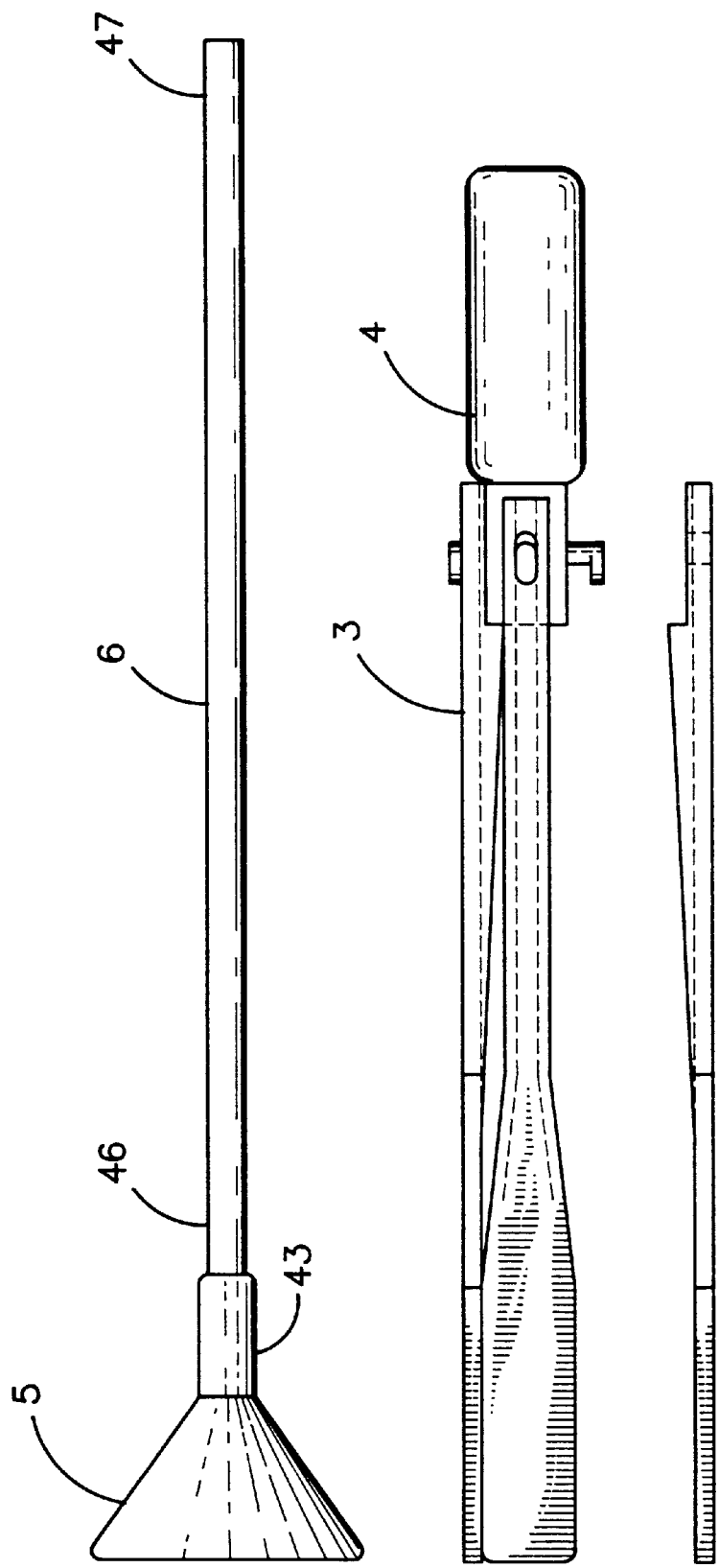
FIG. 6 shows the application cone and application rod forming part of this invention. Also depicted are the insertion handle and insertion wands.

FIG. 6 depicts application cone 5 attached to application rod 6. Application rod 6 is a rigid or semi-rigid rod with a circular cross-section. Application rod 6 has rod distal end 46 and rod proximal end 47. As shown by FIG. 6, application rod 6 has a length greater than the connected combination of insertion wands 3 and insertion handle 4 so that when device 100 is assembled as shown in FIG. 1, rod proximal end 47 will protrude from insertion handle 4. Rod distal end 46 is attached to cone 5 at cone attachment end 43. Application rod 6 is made so that, at least at its proximal end 47, application rod 6 will slidably fit through the tunnel of insertion handle 4. As shown in FIG. 1, graduation markings 49 may be placed on application rod 6 near rod proximal end 47. Graduation markings 49 will assist the operator in determining when the device has been properly placed over the fetal head.

Figure 7:
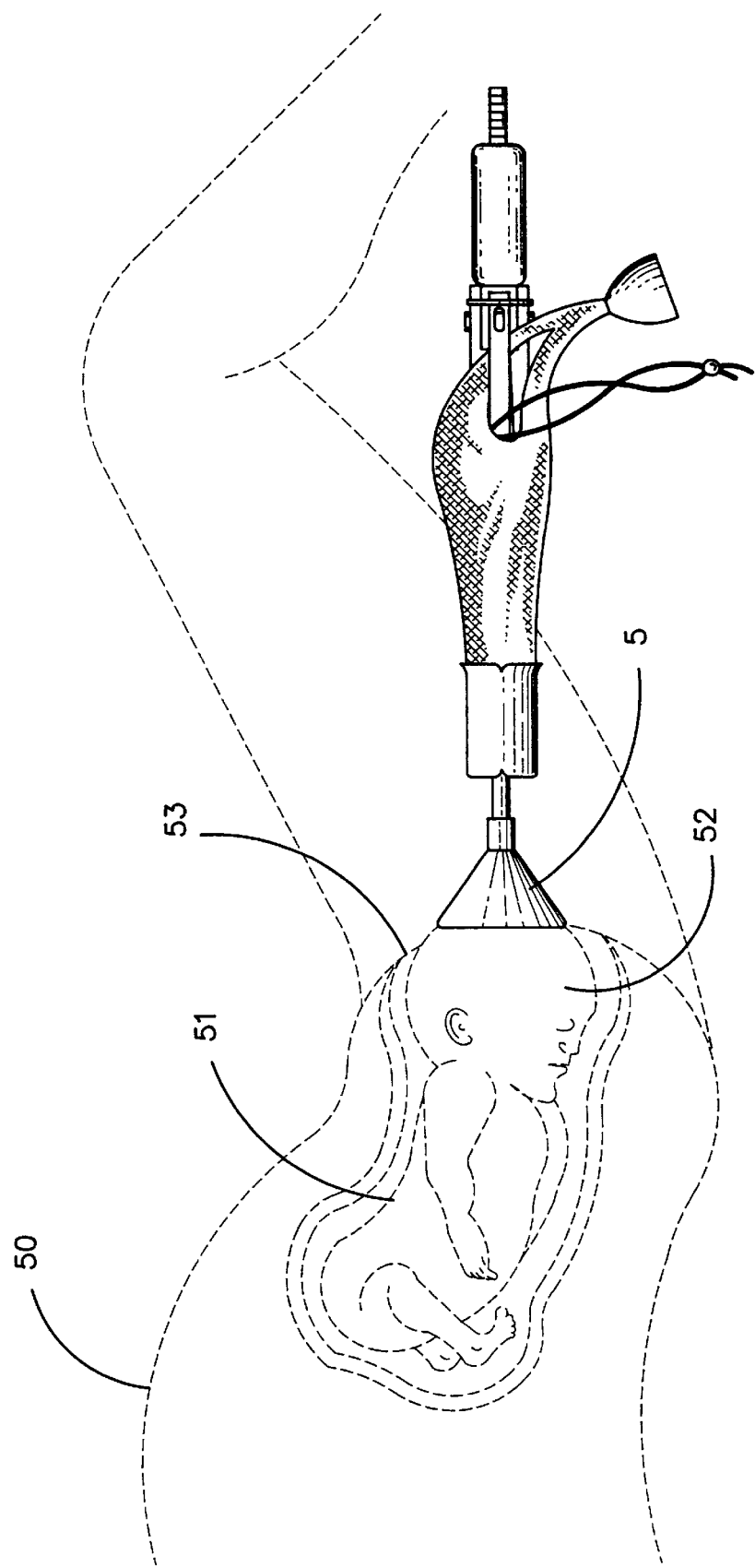
FIGS. 7–10 are cut-away views of a mother with a fetus. The figures depict various stages of the use of the apparatus in vaginal delivery.

The operation of the device will now be described with reference to FIGS. 7–10. FIGS. 7–10 are cut-away views of mother 50 with fetus 51 ready for delivery. The operator of the devices, usually a physician, will prepare device 100 for insertion so that device 100 is configured as shown in FIG. 1. The operator folds cone 5 and inserts cone 5 into introitus 53 so that cone 5 can open up and engage fetal head 52 as shown in FIG. 7.

Figure 8:
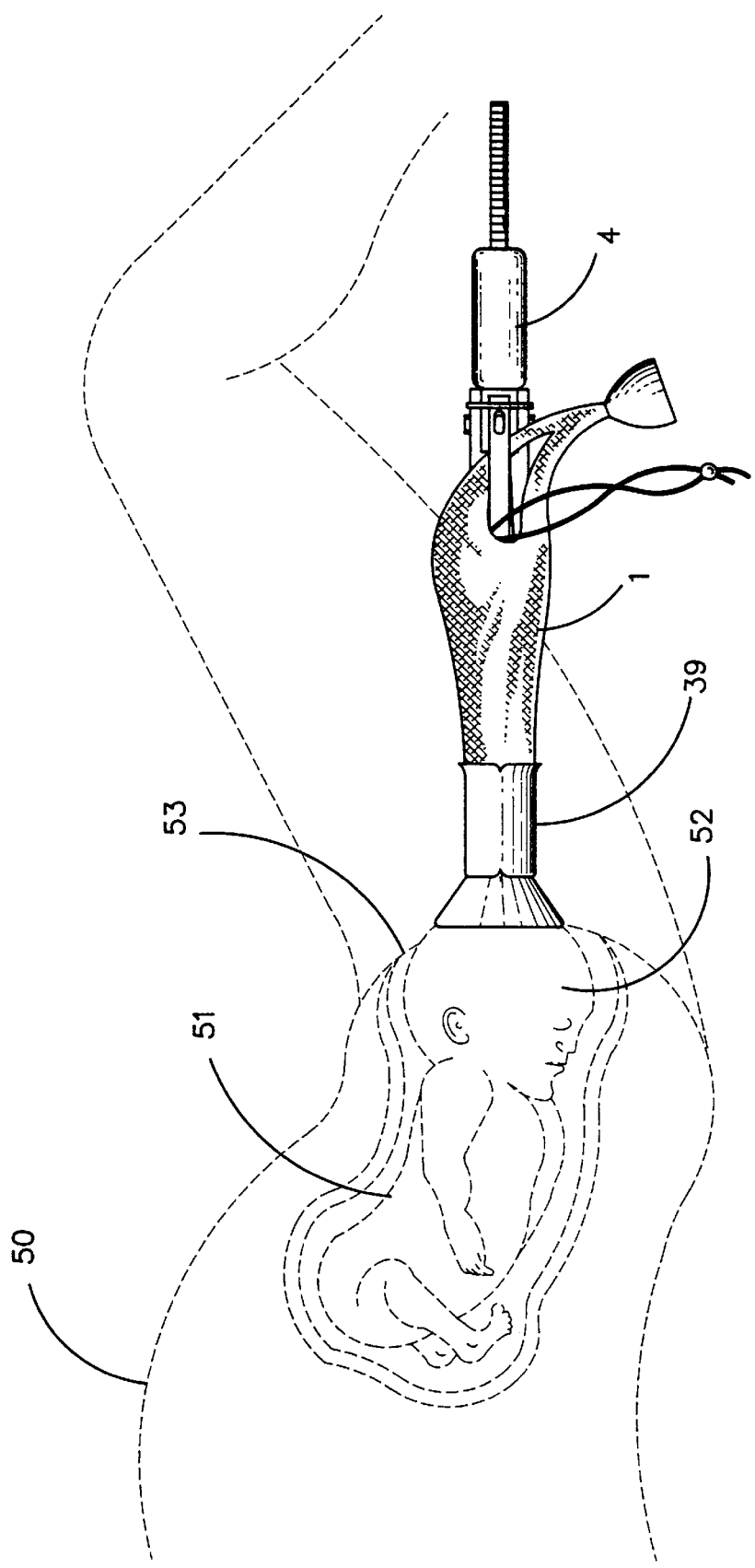

Ensuring that open first end 11 and insertion wands 3 are contained within insertion sleeve 39, as shown in FIG. 1, the operator next inserts at least a portion of insertion sleeve 39 into introitus 53, as shown in FIG. 8. The operator can now, by applying force into the birth canal at insertion handle 4, slide elongated member 1 through insertion sleeve 39 into the birth canal of said mother. The operator then slides insertion sleeve 39 rearward out from introitus 53 and cuts and removes insertion sleeve 39.

Figure 9:
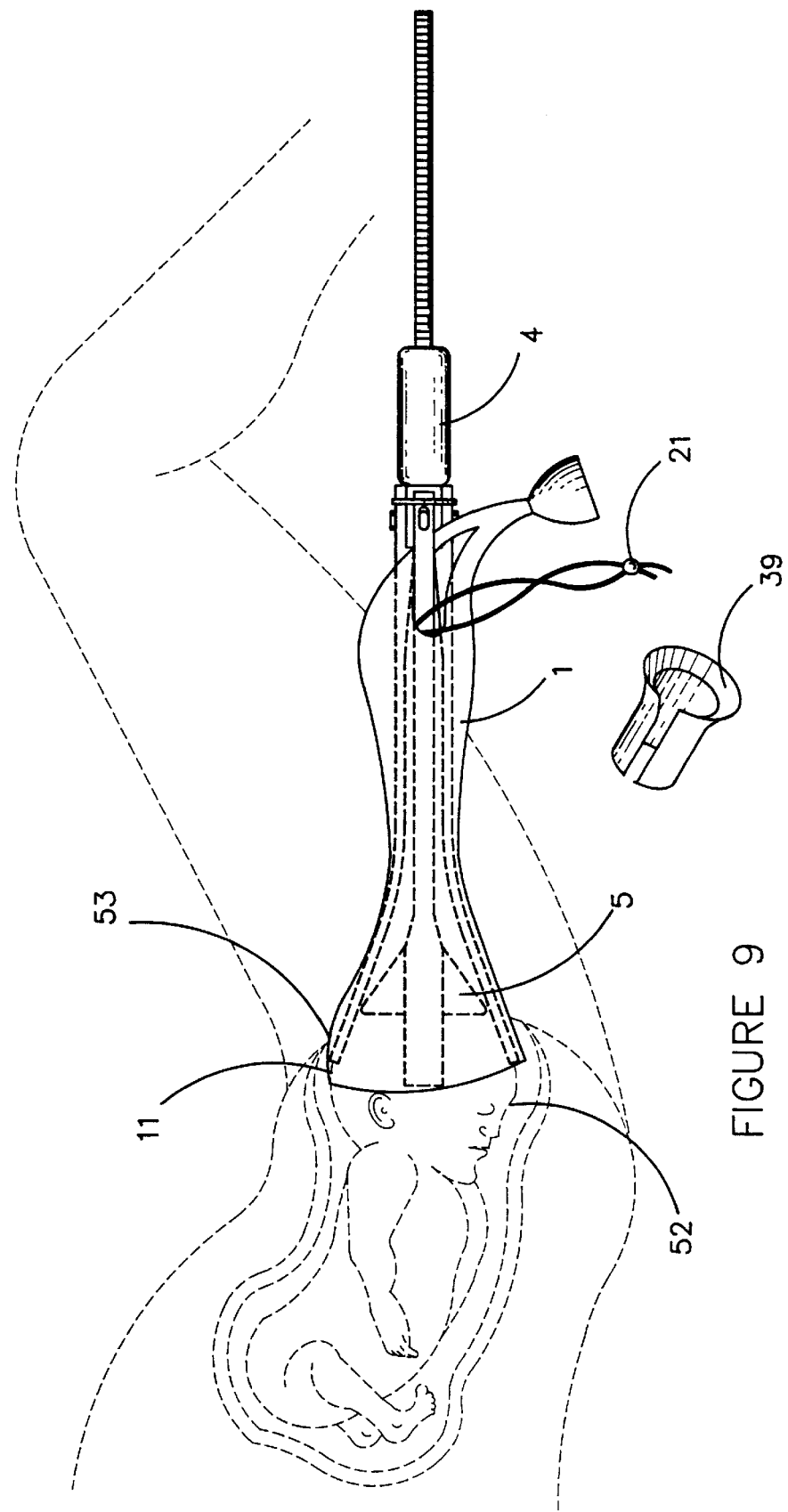

As depicted in FIG. 9, the operator next pushes forward (into the birth canal) on insertion handle 4 while maintaining cone 5 engaged against head 52 so that cone 5 guides open first end 11 of elongated member 1 over head 52. Although open first end 11 is optimally positioned below the mentum head 52 prior to traction being applied, it is only necessary that open first end 11 be below the widest cross-section of head 52, as presented. Pulling on fastener 21, the operator tightens restricting means 13 so that open first end 11 is fitted about head 52 while continuing to apply forward force to insertion handle 4.

The operator pulls rearward on insertion handle 4 to remove insertion handle 4 with attached insertion wands 3 while maintaining tension on restricting means 13. Continuing to maintain tension, the operator removes application rod 6 with cone 5.

Figure 10:
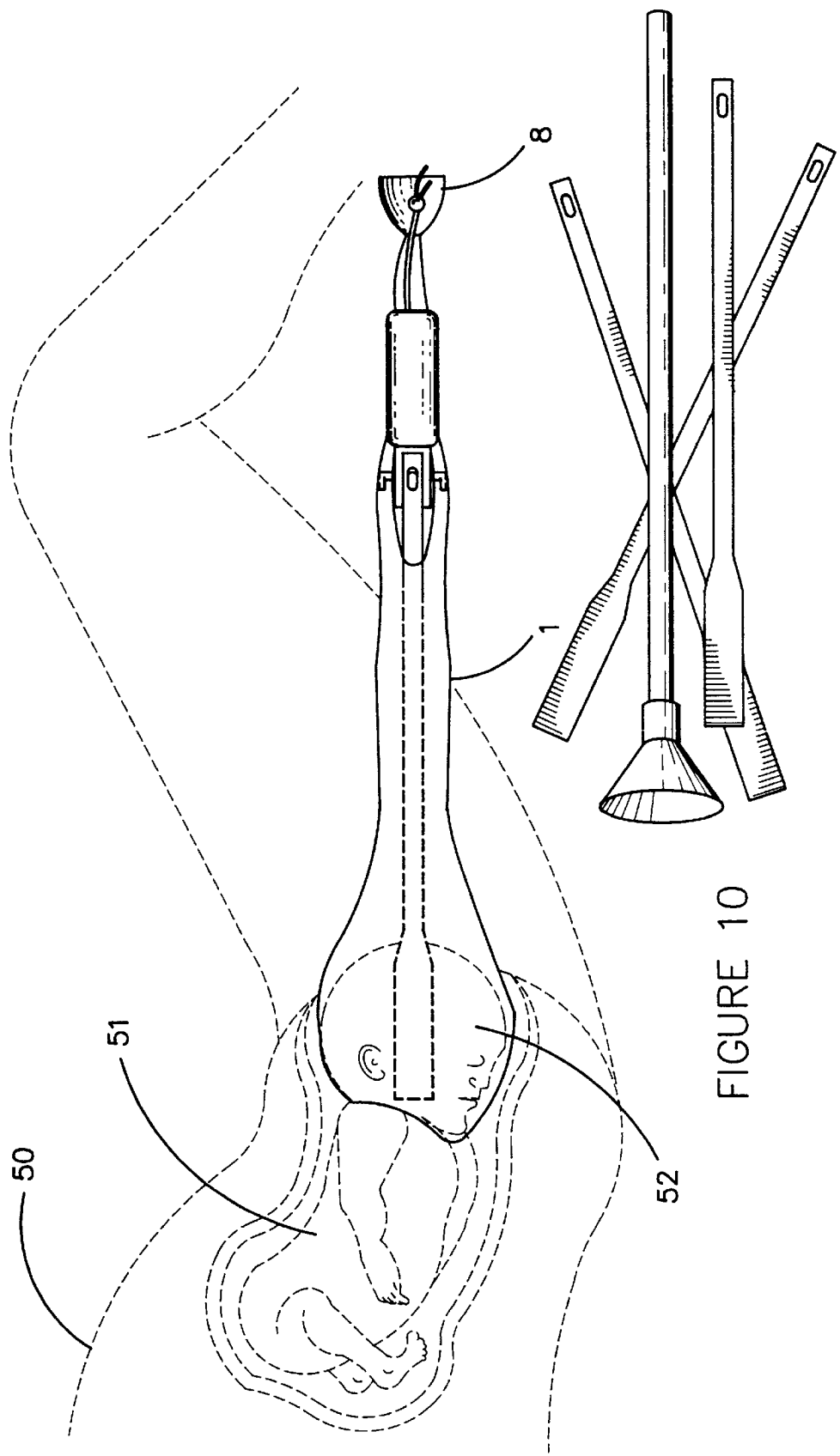
Figure 16A:
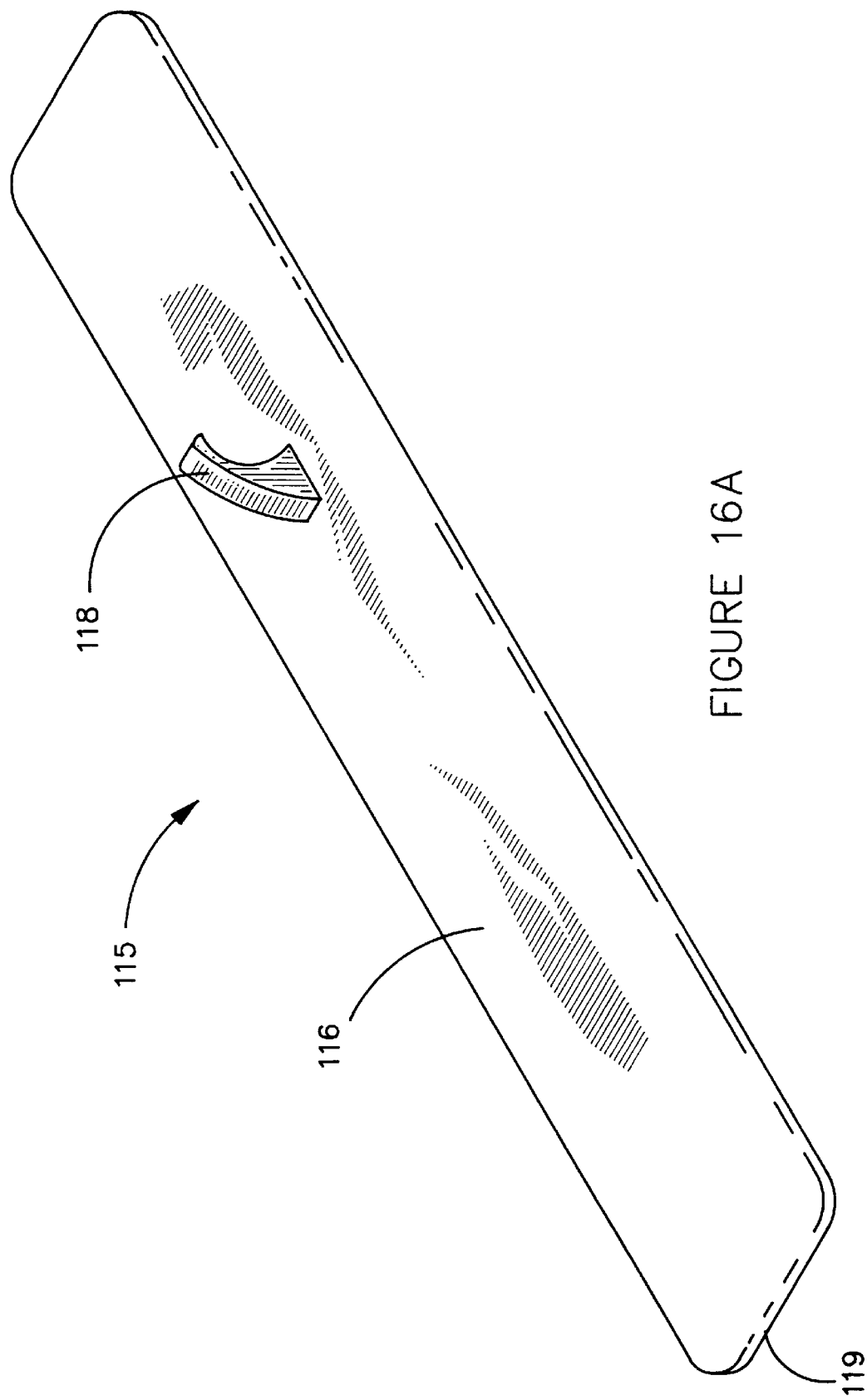
FIG. 16A is a perspective view of a preferred embodiment of an applicator.
Figure 16B:
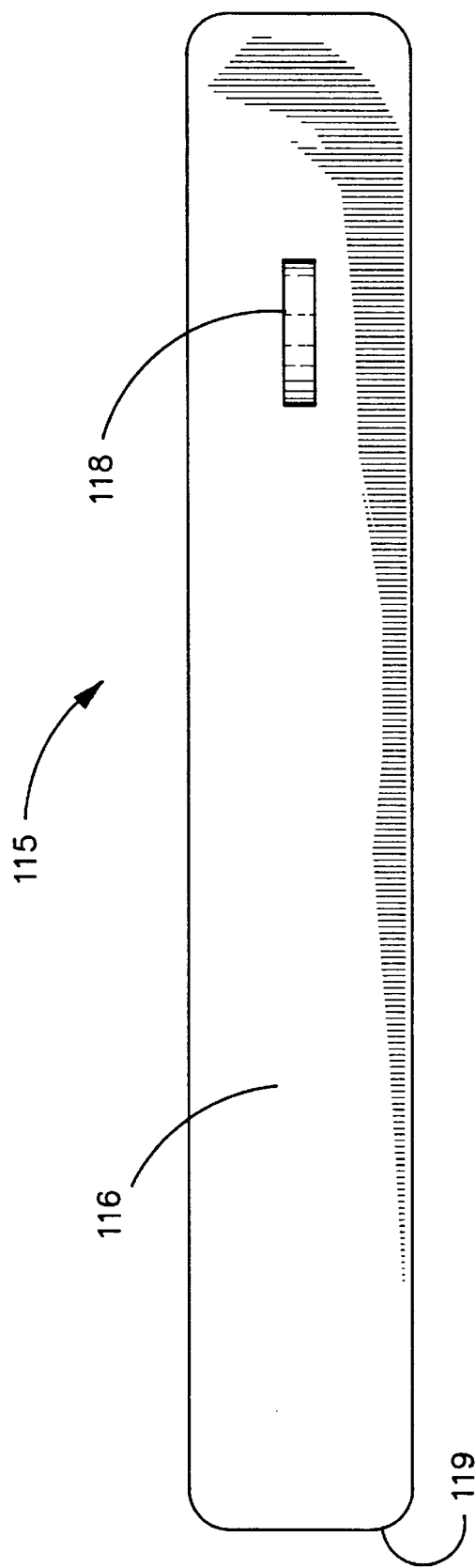
FIG. 16B is a top view of a preferred embodiment of an applicator.
Figure 16C:
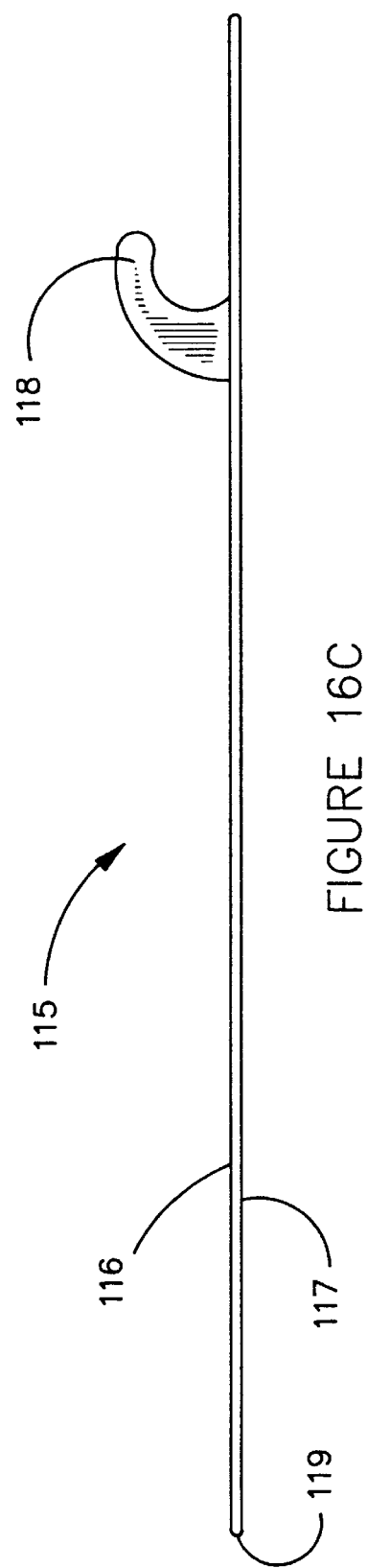
FIG. 16C is a side view of a preferred embodiment of an applicator.

Elongated member 1 is now over head 52 as shown in FIG. 10. The operator pulls rearward on traction handle 8 while maintaining tension on restricting means 13 so that the braid material of elongated member 1 will axially grip head 52 as shown in FIG. 10. Once axial gripping is initiated, the operator no longer needs to maintain tension on restricting means 13. The operator continues to pull on traction handle 8 to extract fetus 51 from mother 50 and complete delivery. Constant or intermittent traction can be applied to facilitate the head's passage through the birth canal.

Device 100 can be adapted to facilitate various complications of delivery. For example, depending on the presentation of the fetus, the operator can attach insertion wands 3 of varying lengths, onto insertion handle 4 so as to properly place open first end 11 over the fetal head.

The invention should be understood to assist in the delivery of any type of fetus, not only human fetuses. In other words, the embodiments disclosed would also be applicable to veterinary obstetrics in deliveries of such mammals as horses, cattle, and sheep.

Another preferred embodiment of the invention is illustrated in FIGS. 11 through 20. The description of this embodiment is set out below; however, it should be read in view of the foregoing descriptions in this and in previous parent applications, all of which are incorporated by reference into the following, to the extent they are not incompatible therewith.

In this preferred embodiment, elongated member 1 comprises a substantially cylindrical tube of braided monofilament 120 or other suitable material as described above. In this preferred embodiment, the braids are terminated at each end by enclosing their loose ends in a collar 101 or by other similar means.

Drawstring 15, described more fully above, may be positioned so that drawstring looped portion 38 is centrally located on the exterior of elongated member 1. Elongated member 1 is then folded back over itself until drawstring looped portion 38 is positioned at one end of the now folded elongated member 1A. The end of folded elongated member 1A containing drawstring looped portion 38, comprises the mouth 102 of this embodiment of the device for assisting childbirth 100. Folding elongated member 1 creates an outer layer 9 and an inner layer 10 of folded elongated member 1A. Folded elongated member 1A contains an annular space 103 between outer layer 9 and inner layer 10. The end of folded elongated member 1A opposite mouth 102 is open as illustrated in FIG. 13 in order to provide access to annular space 103. Passage may thus be had to the mouth end 104 of the folded elongated member 1A from the exterior of folded elogated member 1A via annular space 103. Drawstring 15 extends from mouth end 104 to the exterior of folded elongated member 1A via annular space 103. It should be noted that the function of annular space 103 would not be compromised if the end of elongated member 1 forming the open end of inner layer 10 were closed or perhaps gathered in a handle such as traction handle 8.

Figure 17:
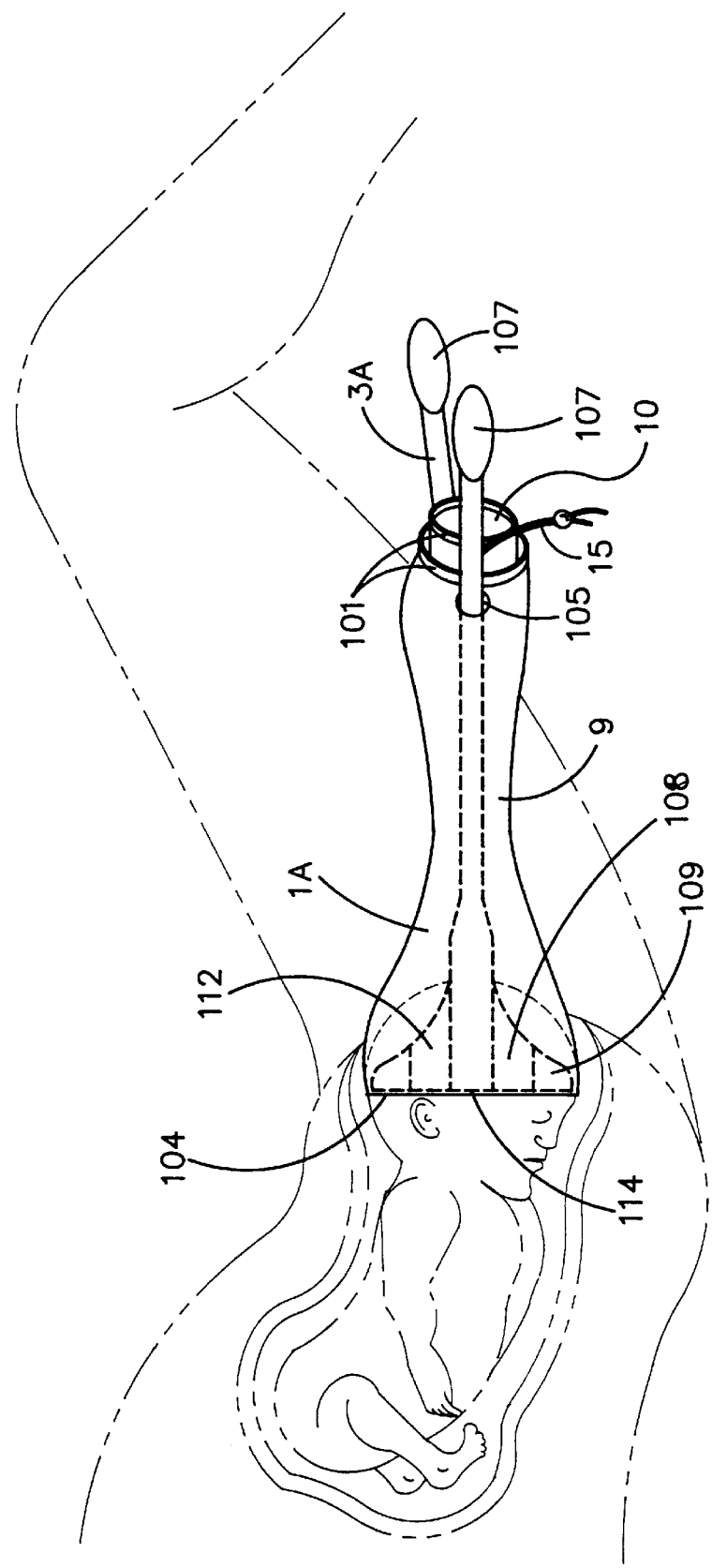
FIG. 17 illustrates a preferred embodiment of folded elongated member being placed over the head of a human fetus using preferred embodiments of insertion wand.
Figure 18:
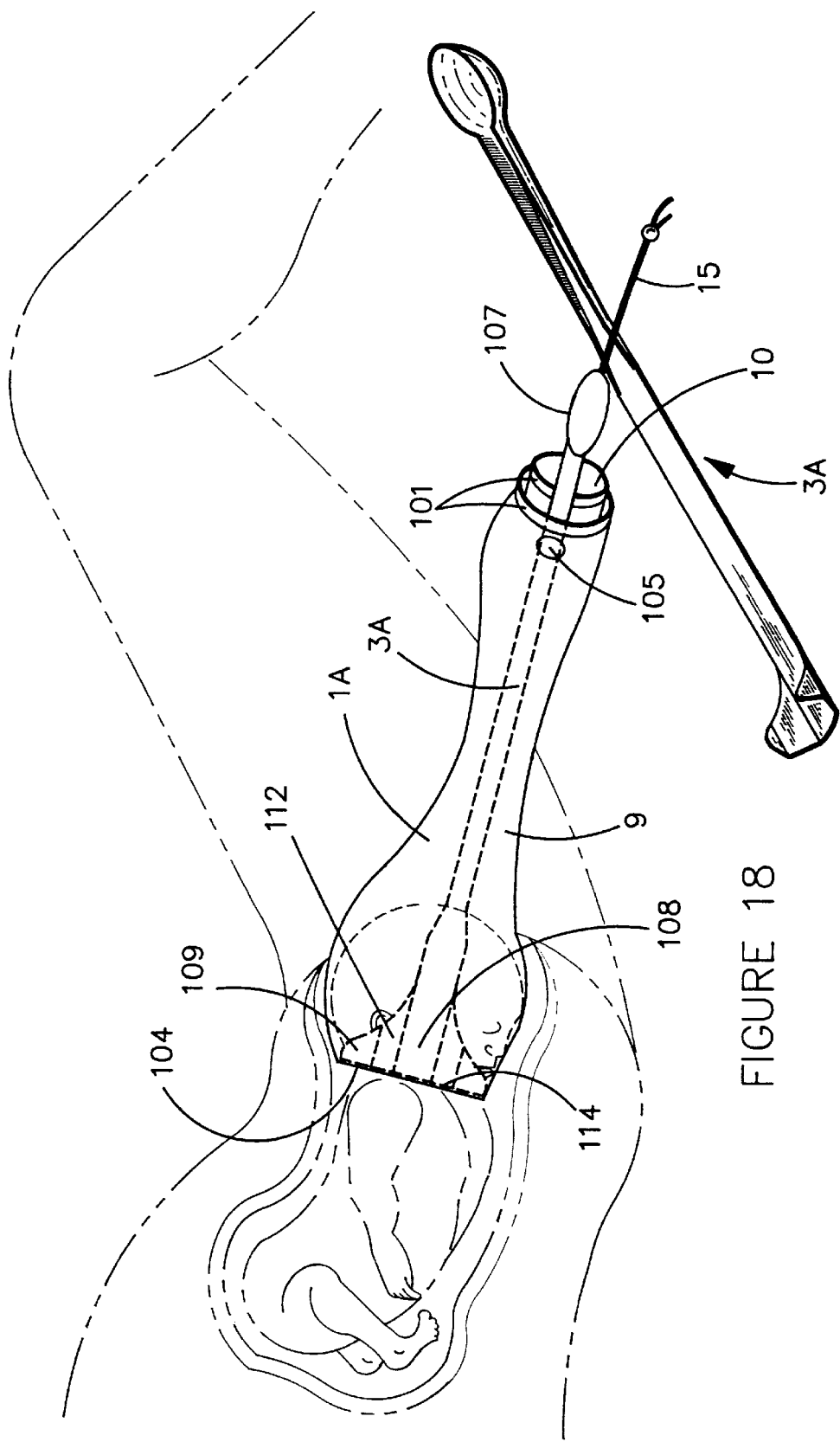
FIG. 18 illustrates a preferred embodiment of folded elongated member after it has been placed over the head of a human fetus using preferred embodiments of insertion wand and after the drawstring has been tightened.
Figure 19:
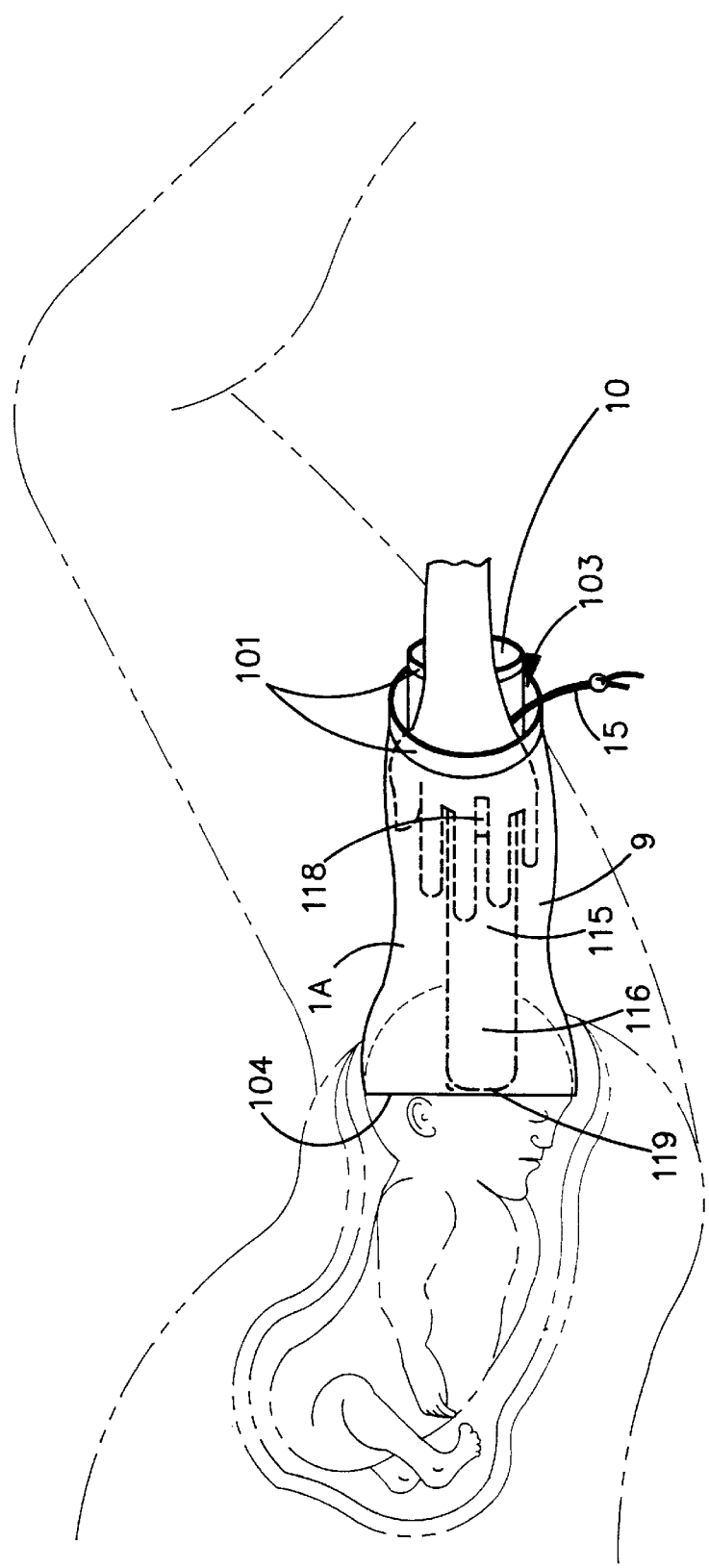
FIG. 19 illustrates a preferred embodiment of folded elongated member being placed over the head of a human fetus using a preferred embodiment of an applicator.
Figure 20:
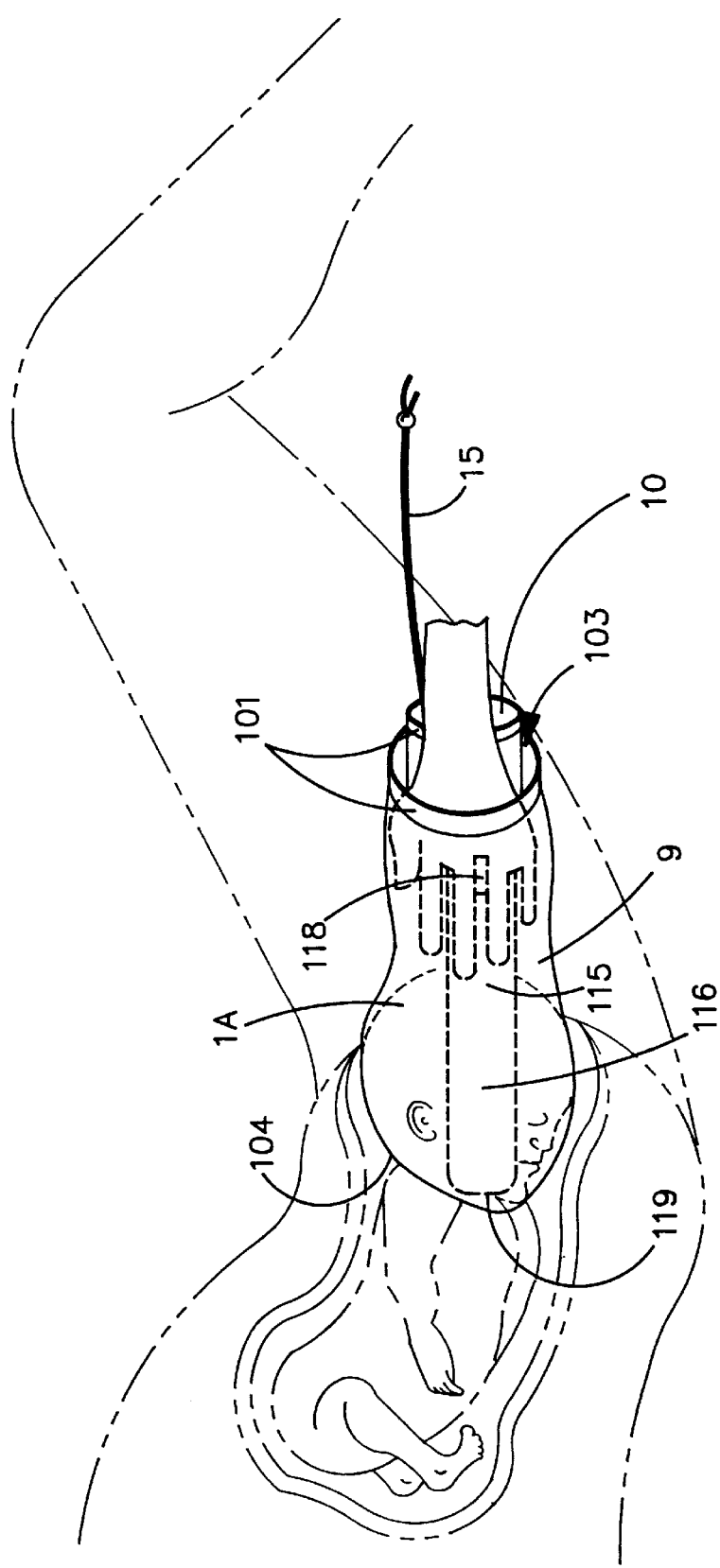
FIG. 20 illustrates a preferred embodiment of folded elongated member after it has been placed over the head of a human fetus using a preferred embodiment of an applicator and after the drawstring has been tightened.

In this preferred embodiment, sheaths 2 may be omitted. Instead of sheaths 2, insertion wands 3A may be placed in annular space 103 as shown in FIGS. 13, 17 and 18. Access may be provided to annular space 103 via the open end of folded elongated member 1A opposite mouth 102. Alternatively, access may be provided via a plurality of windows 105 positioned in outer layer 9. Wands 3A may be inserted through windows 105. The window embodiment may be preferable because it provides a means for presetting the position of wands 3A. When the window embodiment is used, one window 105 should preferably be substantially aligned with the point where drawstring 15 joins drawstring looped portion 38. By positioning a wand 3A (or applicator 115 discussed below) over this point of joinder, the retraction of a portion of the mouth end 104 back toward the operator when the drawstring is tightened may be prevented.

For different reasons, it may be preferable not to use windows 105 to provide access to annular space 103 for wands 3A. It is anticipated that operators may want to rotate wands 3A to some degree as they insert wands 3A between the head of the fetus and the walls of the birth canal to ensure that substantially all of mouth end 104 has been positioned below the chin of the fetus. Using windows 105 to provide access to annular space 103 may inhibit this rotation. In such cases, it may be desirable to gain access to annular space 103 via the open end of folded elongated member 1A opposite mouth 102. In any event, either option may be readily practiced at the professional discretion of those skilled in the art as illustrated in FIGS. 17 and 18.

In a preferred embodiment, wands 3A comprise an elongated shaft 106 having a control end 107 and an application end 108. As shaft 106 approaches application end 108, it should become substantially flat and thin in order to facilitate its insertion between the head of the fetus and the walls of the birth canal. Wands 3A are preferably constructed of a smooth resilient plastic.

In this preferred embodiment, application end 108 is formed of a plurality of hinged sections 109. When hinged sections 109 are in their fully extended position 110, the inner face 111 of application end 108 will be a substantially smooth concave surface. Similarly, the outer face 112 of application end 108 will be a substantially smooth convex surface. The curvature of inner face 111 of application end 108 should approximately conform to the head of a human fetus.

Sections 109 of this preferred embodiment should be hinged to allow them to fold inward when pressure is applied to their outer face 112 and outward when pressure is applied to their inner face 111. One preferred method of hinging sections 109 is to place a resilient flexible adhesive strip 113 (not shown) across inner face 111 of sections 109 (adhesive side down). But for adhesive strip 113, sections 109 would not be connected. Because of the flexible nature of adhesive strip 113, application of pressure to sections 109 will allow them to pivot relative to one another. Contact between hinged sections 109 will prevent them from pivoting beyond fully extended position 110.

In operation, wands 3A will be placed into annular space 103 either through windows 105 or through the open end of folded elongated member 1A opposite mouth end 104. Wands 3A may be used to insert this embodiment of device for assisting childbirth 100 into the birth canal. As wands 3A are inserted into the birth canal, the walls of the birth canal will press against the outer face 112 of application end 108, causing hinged sections 109 to fold inward. This will facilitate the insertion of wands 3A into the birth canal. When wands 3A reach the head of the fetus, the curvature of the head of the fetus will force hinged sections 109 outward, until they reach fully extended position 110.

At this point, continued forward pressure on wands 3A will force them between the head of the fetus and the walls of the birth canal. Wands 3A should be advanced until the leading edge 114 of application end 108 is past the chin of the fetus.

One problem that may arise in operation of the invention, is that portions of mouth end 104 between wands 3A may not advance as far as leading edge 114. The greater the distance between wands 3A, the more likely this problem is to arise. To avoid the problem, the space between wands 3A should be minimized. The inventor anticipates using a pair of wands 3A each of whose leading edge 114 is approximately 16 to 18 cm long and which comprises an arc of about 135° when application end 108 is in fully extended position 110. It is expected that best results will be obtained when leading edge 114 is at least about ⅜ the circumference of the head of a human fetus. It is the inventor's understanding that the circumference of the heads of term fetuses averages about 39 cm±1 cm.

In addition to the hinged wand embodiment of the invention described above, the inventor contemplates another means for positioning mouth end 104 of folded elongated member 1A over the chin of the fetus. In this embodiment, the operator, usually a physician or midwife, will place his hands in mouth end 104 of folded elongated member 1A via annular space 103. Using his hands, he will advance mouth end 104 of folded elongated member 1A to the head of the fetus. Of course, if the operator could place his hands between the head of the fetus and the birth canal walls, he would use his hands to extract the fetus. In the situations where the invention is needed, this is generally not possible. Thus, another device must be used to advance mouth end 104 beyond the chin of the fetus.

The device contemplated by the inventor is an applicator 115 comprising an elongated flat thin plate having an outer face 116 and an inner face 117. Applicator 115 is similar in shape to a tongue depressor but with flat ends and is preferably made of a smooth resilient plastic. Extending from outer face 116 of applicator 115 is a hand engaging hook 118. Hook 118 is configured to engage the hand of the operator at the point where the fingers join the palm when applicator 115 is positioned on the palm side of the operator's hand. Applicator 115 should be configured so that when hook 118 engages the operator's hand, the leading edge 119 of applicator 115 extends at least the length of the skull of a human fetus beyond the end of the fingers of the operator.

The operator uses applicator 115 to advance mouth end 104 past the chin of the fetus by placing leading edge 119 of applicator 115 in mouth end 104 of folded elongated member 1A. Using hook 118, the operator may use his hands to force applicator 115 between the head of the fetus and the birth canal walls. By continuing to apply force, the operator may advance applicator 115 until its leading edge 119 is past the chin of the fetus. Of course, when leading edge 119 has advanced beyond the chin of the fetus, it will have advanced a portion of mouth end 104 beyond the chin of the fetus as well. This process may be repeated until all of mouth end 104 is beyond the chin of the fetus.

When mouth end 104 has been appropriately positioned over the chin of the fetus, drawstring 15 should be tightened slightly. Tightening drawstring 15 serves two principal purposes. First, it allows wands 3A to be removed without retracting mouth end 104 back over the chin of the fetus. Second, it will facilitate the initiation of axial gripping.

Once applicator 115 or wands 3A have been removed and drawstring 15 has been tightened, the operator will pull on the end of inner layer 10, exerting a longitudinal force on folded elongated member 1A. This will cause the elongated member to exert an axial gripping force on the head of the fetus in the same way that "Chinese handcuff" novelty items exert an axial gripping force on the finger of the user. Once axial gripping has been initiated, tension need not, and preferably should not, be maintained on drawstring 15. Because of the axial gripping, the force of the traction will be evenly distributed over the entire head of the fetus.

After the fetus has been extracted from the birth canal, or if at some time prior to that, it becomes necessary to remove device for assisting childbirth 100, this embodiment is particularly well suited for rapid removal. The operator need only pull on the end of outer layer 9 without pulling on inner layer 10. This will cause device for assisting childbirth 100 to peel away from the head of the fetus.

There are, of course, other alternate embodiments which are obvious from the foregoing descriptions of the invention which are intended to be included within the scope of the invention as defined by the following claims.

I claim:

1. A device for assisting the delivery of a fetus comprising:

a substantially cylindrical elongated member constructed of a braid material comprising loosely interwoven fibers, wherein said elongated member is folded back upon itself to form an inner layer, an outer layer, an annular space defined by said inner layer and said outer layer, and a mouth sized to receive the head of a fetus, said braid material configured to exert an axial gripping force on the head of a fetus positioned within said mouth of said elongated member when a longitudinal force is exerted on said elongated member;

a means for positioning said mouth over the head of a fetus comprising at least one insertion wand comprising an elongated shaft having a control end and a substantially smooth thin application end, said application end comprising a plurality of hinged sections having a fully extended position, said application end having an inner face, an outer face and a leading edge, said application end sized to fit between the head of a fetus and the walls of the birth canal during delivery when said hinged sections are in said fully extended position; and a means for restricting the size of said mouth after it has been placed over the head of a fetus.

2. A device for assisting the delivery of a fetus according to claim 1 wherein said inner face of said applicator end is curved to substantially conform to the curvature of the head of a human fetus when said hinged sections are in said fully extended position.

3. A device for assisting the delivery of a fetus according to claim 1 wherein said leading edge is of sufficient length to encompass at least about three eighths of the circumference of the head of a human fetus when said hinged sections of said application end are in said fully extended position.

4. A device for assisting the delivery of a fetus according to claim 1 wherein at least one said wand is removably positioned within said annular space such that said leading edge of said application end is positioned at said mouth of said elongated member.

5. A device for assisting the delivery of a fetus according to claim 1 wherein said means for restricting the size of said mouth comprises a drawstring having a looped portion, said drawstring looped portion positioned at said mouth.

6. A device for assisting the delivery of a fetus according to claim 5 wherein said drawstring is positioned within said annular space.

7. A device for assisting the delivery of a fetus according to claim 1 wherein said fibers comprise monofilament strands.

8. A device for assisting the delivery of a fetus comprising:
- a substantially cylindrical elongated member constructed of a braid material comprising loosely interwoven fibers, said elongated member having an open end comprising a mouth, said mouth sized to receive the head of a fetus, said braid material configured to exert an axial gripping force on the head of a fetus positioned within said mouth of said elongated member when a longitudinal force is exerted on said elongated member;
- a means for positioning said mouth over the head of a fetus comprising at least one insertion wand comprising an elongated shaft having a control end and a substantially smooth thin application end, said application end comprising a plurality of hinged sections having a fully extended position, said application end having an inner face, an outer face and a leading edge, said application end sized to fit between the head of a fetus and the walls of the birth canal during delivery when said hinged sections are in said fully extended position; and
- a means for restricting the size of said mouth after it has been placed over the head of a fetus.

9. A device for assisting the delivery of a fetus according to claim 8 wherein said mouth is formed by folding said elongated member back upon itself, said folded end of said elongated member comprising said mouth.

10. A device for assisting the delivery of a fetus according to claim 9 wherein said folded elongated member has an inner layer and an outer layer, said inner layer and said outer layer defining an annular space therebetween.

11. A device for assisting the delivery of a fetus according to claim 10 wherein said means for restricting the size of said mouth comprises a drawstring having a looped portion, said drawstring looped portion positioned at said mouth.

12. A device for assisting the delivery of a fetus according to claim 11 wherein said drawstring is positioned within said annular space.

13. A device for assisting the delivery of a fetus according to claim 10 wherein at least one said wand is removably positioned within said annular space such that said leading edge of said application end is positioned at said mouth of said elongated member.

14. A device for assisting the delivery of a fetus according to claim 8 wherein said inner face of said applicator end is curved to substantially conform to the curvature of the head of a human fetus when said hinged sections are in said fully extended position.

15. A device for assisting the delivery of a fetus according to claim 8 wherein said leading edge is of sufficient length to encompass at least about three eighths of the circumference of the head of a human fetus when said hinged sections of said application end are in said fully extended position.

16. A device for assisting the delivery of a fetus according to claim 8 wherein said fibers comprise monofilament strands.

17. A device for assisting the delivery of a fetus comprising:
- a substantially cylindrical elongated member constructed of a braid material comprising loosely interwoven fibers, wherein said elongated member is folded back upon itself to form an inner layer, an outer layer, an annular space defined by said inner layer and said outer layer, and a mouth sized to receive the head of a fetus, said braid material configured to exert an axial gripping force on the head of a fetus positioned within said mouth of said elongated member when a longitudinal force is exerted on said elongated member;
- a means for positioning said mouth over the head of a fetus comprising at least one applicator comprising an elongated flat thin plate having an inner face, an outer face and a leading edge, said applicator further comprising a hand engaging hook extending from said outer face; and
- a means for restricting the size of said mouth after it has been placed over the head of a fetus.

18. A device for assisting the delivery of a fetus according to claim 17 wherein at least one said applicator is removably positioned within said annular space such that said leading edge of said applicator is positioned at said mouth of said elongated member.

19. A device for assisting the delivery of a fetus according to claim 17 wherein said means for restricting the size of said mouth comprises a drawstring having a looped portion, said drawstring looped portion positioned at said mouth.

20. A device for assisting the delivery of a fetus according to claim 19 wherein said drawstring is positioned within said annular space.

21. A device for assisting the delivery of a fetus according to claim 17 wherein said fibers comprise monofilament strands.

22. A device for assisting the delivery of a fetus comprising:
- a substantially cylindrical elongated member constructed of a braid material comprising loosely interwoven fibers, said elongated member having an open end comprising a mouth, said mouth sized to receive the head of a fetus, said braid material configured to exert an axial gripping force on the head of a fetus positioned within said mouth of said elongated member when a longitudinal force is exerted on said elongated member;
- a means for positioning said mouth over the head of a fetus comprising at least one applicator comprising an elongated flat thin plate having an inner face, an outer face and a leading edge, said applicator further comprising a hand engaging hook extending from said outer face; and
- a means for restricting the size of said mouth after it has been placed over the head of a fetus.

23. A device for assisting the delivery of a fetus according to claim 22 wherein said mouth is formed by folding said elongated member back upon itself, said folded end of said elongated member comprising said mouth.

24. A device for assisting the delivery of a fetus according to claim 23 wherein said folded elongated member has an inner layer and an outer layer, said inner layer and said outer layer defining an annular space therebetween.

25. A device for assisting the delivery of a fetus according to claim 24 wherein said means for restricting the size of said mouth comprises a drawstring having a looped portion, said drawstring looped portion positioned at said mouth.

26. A device for assisting the delivery of a fetus according to claim 25 wherein said drawstring is positioned within said annular space.

27. A device for assisting the delivery of a fetus according to claim 24 wherein at least one said applicator is removably positioned within said annular space such that said leading edge of said applicator is positioned at said mouth of said elongated member.

28. A device for assisting the delivery of a fetus according to claim 22 wherein said fibers comprise monofilament strands.

* * * * *